United States Patent [19]
Kikawada et al.

[11] Patent Number: 5,447,149
[45] Date of Patent: Sep. 5, 1995

[54] ADJUSTABLE POSITION FIXING APPARATUS FOR INSTRUMENT AND THE LIKE

[75] Inventors: Toru Kikawada; Minoru Kawai, both of Hamamatsu, Japan

[73] Assignee: Kabushiki Kaisha Eier, Shizuoka, Japan

[21] Appl. No.: 126,598

[22] Filed: Aug. 25, 1993

[30] Foreign Application Priority Data

Mar. 29, 1993 [JP] Japan .................................. 5-014922

[51] Int. Cl.⁶ .................................................. A61B 17/02
[52] U.S. Cl. ................................... 600/229; 248/276.1
[58] Field of Search ............... 606/1, 59, 57; 248/276, 248/248, 109, 160; 128/20, DIG. 26, 17, 3, 18

[56] References Cited

U.S. PATENT DOCUMENTS

| | | | |
|---|---|---|---|
| 3,096,962 | 7/1963 | Meijs | 248/276 |
| 3,858,578 | 1/1975 | Milo et al. | 128/20 |
| 4,143,652 | 3/1979 | Meier et al. | 128/20 |
| 4,457,300 | 7/1984 | Budde et al. | 128/20 |
| 4,573,452 | 3/1986 | Greenberg | 128/20 |
| 4,867,404 | 9/1989 | Harrington et al. | 248/276 X |
| 5,201,325 | 4/1993 | McEwen et al. | 128/20 X |
| 5,284,130 | 2/1994 | Ratliff | 128/20 |

*Primary Examiner*—Peter A. Aschenbrenner
*Attorney, Agent, or Firm*—Darby & Darby

[57] ABSTRACT

An adjustable position fixing apparatus for fixing instruments such as an endoscope and an illuminator in a desired spatial position is provided. The adjustable position fixing apparatus for an instrument and the like comprises a cylinder communicating with a pressure fluid supplying machine, such as a compressor, through a switching device, a mount member for mounting an instrument and the like thereon, and an adjustable bending arm portion through which a linear element such as a wire extends. The arm portion is disposed between the cylinder and the mount member over an entire area or a part thereof. One end of the linear element is attached to a reciprocating rod of the cylinder and the other end is attached to the mount member.

8 Claims, 2 Drawing Sheets

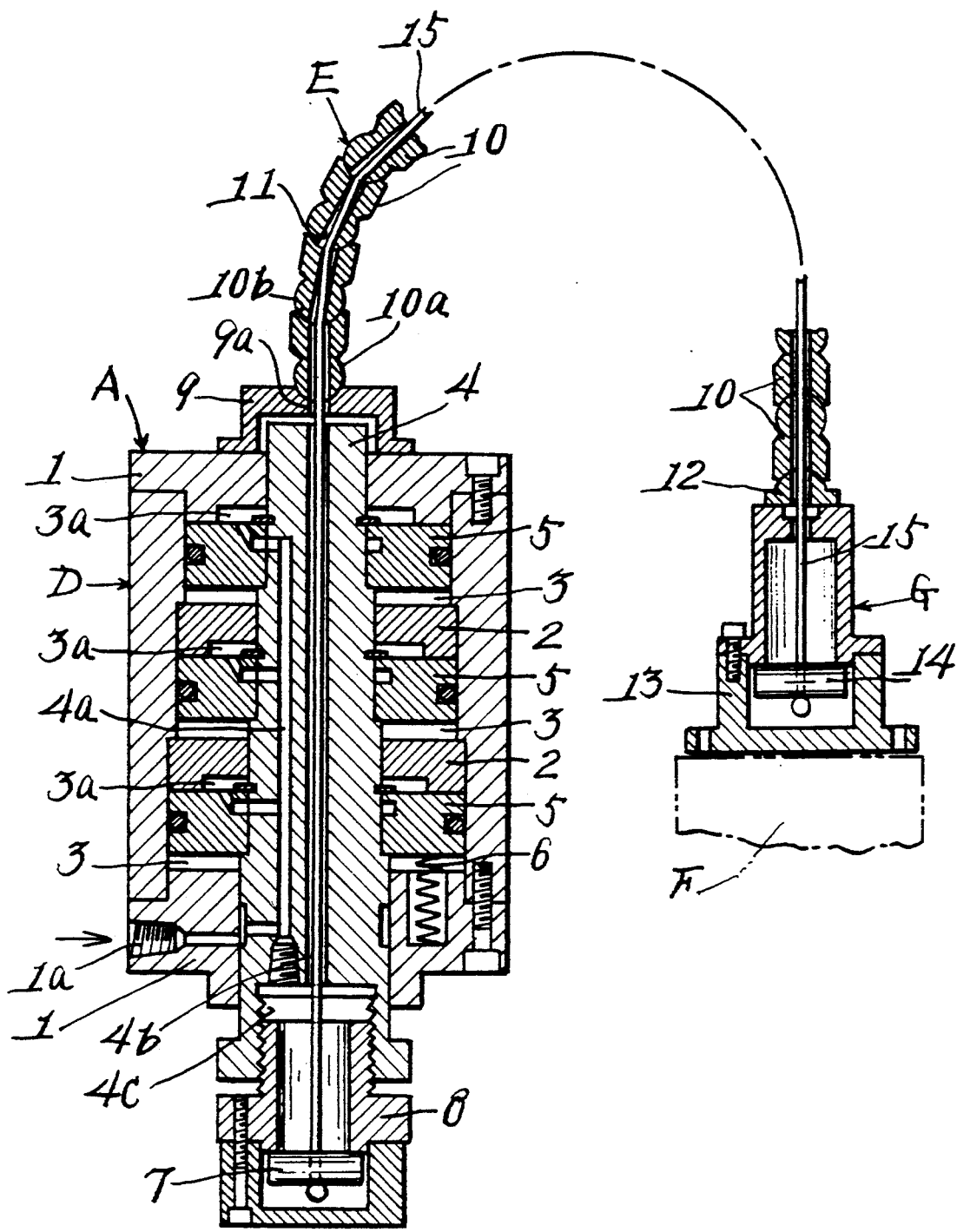

ADJUSTABLE POSITION FIXING APPARATUS FOR INSTRUMENT AND THE LIKE

BACKGROUND OF THE INVENTION

This invention relates to an adjustable position fixing apparatus for fixing an instrument and the like in a desired spatial position.

As a conventional art, there is a brain spatula fixing device used for maintaining an opening condition of a cutout-head portion in a brain surgery operation for the purpose of obtaining an operating space. According to this conventional brain spatula fixing device, connected pieces, through which a wire extends, are disposed between a brain spatula supporting portion at a distal end thereof and an operating portion thereof. One end of the wire is attached to the brain spatula supporting portion, and the other end is attached to an eccentric end of a retainer element fixedly mounted on a handle shaft. The operating portion is fixedly secured to a head holder and an arm by means of a C-clamp, and the handle is rotated, while pressing the operating portion, with the brain spatula supporting portion at the distal end held in a desired position, such that the wire is tensioned in order to fix the brain spatula in a desired spatial position.

However, this conventional brain spatula fixing apparatus has the following drawbacks. That is, since it is required to rotate the handle, while pressing the operating portion, with the brain spatula supporting portion kept held in a desired position, it is difficult to perform these procedures only by its operator. Moreover, since it is designed such that the eccentric end of the retainer element is rotated in accordance with the rotation of the handle in order to cause the wire to be tensioned, a strong force for rotating the handle is required. Accordingly, there is a possibility that the brain spatula supporting portion (namely the brain spatula) tends to move during the rotational operation of the handle. This is of course very dangerous for a surgical operation.

SUMMARY OF THE INVENTION

It is therefore an object of the present invention to provide a fixing apparatus which is capable of fixing an instrument and the like in a desired position by means of a simple operation.

According to the present invention, there is provided an adjustable position fixing apparatus for an instrument and the like comprising a cylinder communicating with a pressure fluid supplying machine, such as a compressor, through switch means, a mount member for mounting an instrument and the like thereon, an adjustable bending arm portion through which a linear element such as a wire extends, the arm portion being disposed between the cylinder and the mount member over an entire area or a part thereof, one end of the linear element being attached to a reciprocating rod of the cylinder and the other end being attached to the mount member.

BRIEF DESCRIPTION OF THE DRAWINGS

The accompanying drawings show embodiments of an adjustable position fixing apparatus according to the present invention for an instrument and the like.

FIG. 2 is an enlarged vertical cross-sectional view of an important part of FIG. 1.

BEST MODE FOR PRACTICING THE INVENTION

[FIRST EMBODIMENT]

Figure 1:
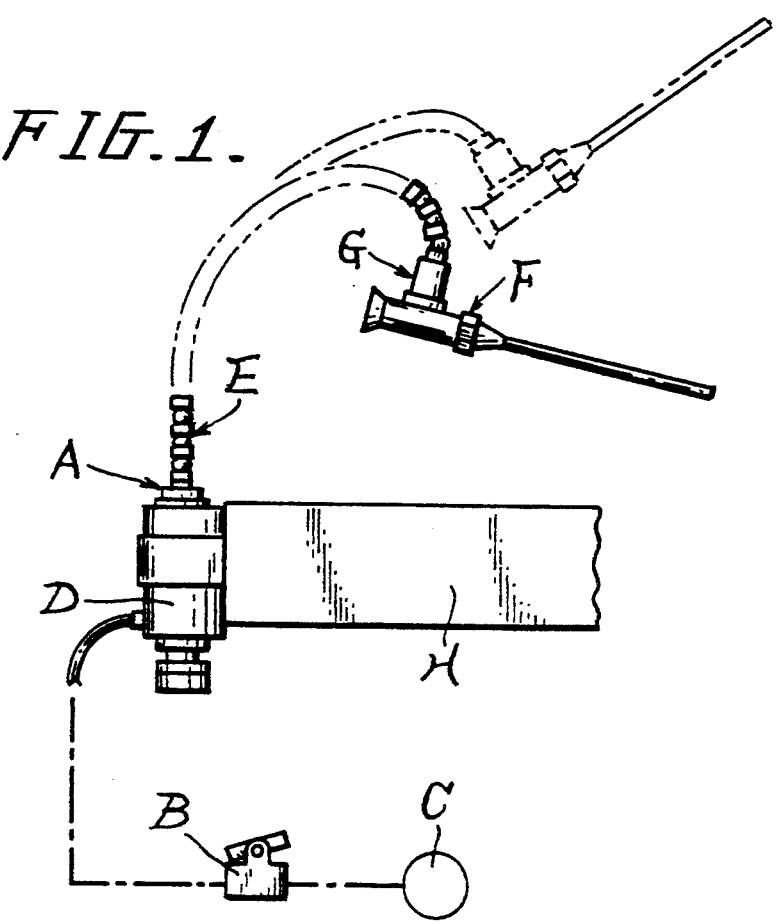
FIG. 1 is an overall view of a first embodiment.

An adjustable position fixing apparatus represented by reference numeral A in the drawings comprises a cylinder D communicating with a pressure fluid supplying machine C, such as a compressor, a pressure pump and the like, through a switching device B, an adjustable bending arm portion E, and a mount member G for an instrument F such as an endoscope or the like.

The cylinder D has a hollow interior closed by upper and lower cover plates 1 and 1. This hollow interior is divided, by two partition walls 2, 2, into three parts to define hollow chambers 3, 3. A reciprocating rod 4 is disposed within the cylinder D such that the rod 4 extends through the respective hollow chambers 3, 3 and also through the upper and lower cover plates 1, 1. Pistons 5, 5 are fixed to the reciprocating rod 4 such that they are located respectively in the hollow chambers 3, 3. A spring 6 is provided between the lower cover plate 1 and one of the pistons 5 in its biased condition. A flow channel 4a is formed longitudinally in the reciprocating rod 4 such that the channel 4a communicates with spaces 3a, 3a formed respectively between the pistons 5, 5 and the upper cover plate 1 and respective partition walls 2, 2. Also, the flow channel 4a is in communication with a supply port 1a which is formed in the lower cover plate 1 and connected to the switching device B and pressure fluid supplying machine C. The reciprocating rod 4 is provided at its lower end with a female-threaded portion 4c which is in communication with a through-hole 4b extending in the reciprocating direction. An adjustment handle 8 retaining an attachment 7 is in threaded engagement with the female-threaded portion 4c. A receiving seat 9 is fixedly secured to an upper surface of the upper cover plate 1 of the cylinder D. The adjustable arm portion E is mounted on the receiving seat 9.

The adjustable arm portion E is composed of a plurality of pieces 10. One end face of each piece 10 is defined as a convexly curved round surface 10a, and the other end face is defined as a concavely curved round surface 10b. Each piece 10 is further provided therein with a through-hole 11 opening to the end faces. The pieces 10 are interconnected one after another such that the convexly curved round surface 10a of one piece is in contact with the concavely curved round surface 10b of its adjacent piece. That piece 10 located at one end of the connected pieces 10 is in abutment relation to the receiving seat 9 of the cylinder D, while another that piece 10 located at the other end of the connected pieces 10 is in abutment relation to a receiving seat 12 which is firmly secured to the mount member G. The mount member G is provided with a mounting portion 13 for the instrument F such as an endoscope. An attachment 14 is retained by the mount member G. One end of a linear member 15 such as a wire is attached to the attachment 14 on the side of the mount member G. The linear member 15 extends through the through-holes 11 of the respective interconnected pieces 10, 10, a through-hole 9a of the receiving seat 9, and further through the through-hole 4b of the reciprocating rod 4.

The other end of the linear member 15 is attached to the attachment 7 retained by the adjustment handle 8.

With the embodiment thus constructed, the cylinder D is fixedly secured to a support table H such as an operation bed. With the instrument F held in a predetermined spatial position, the illustrated pedal type switching device B, for example, is turned on by a foot to supply a pressure fluid from the pressure fluid supplying machine to the respective spaces 3a, 3a via the supply port 1a of the cylinder D and the flow channel 4a of the reciprocating rod 4, so that the respective pistons 5, 5 are pressed down against the bias of the spring 6, thereby lowering the reciprocating rod 4 to pull the attachment 7 of the adjustment handle 8 to cause the linear element 15 to be tensioned. As a result, the contacting surfaces of the respective pieces 10 composing the adjustable arm portion E which is disposed between the receiving seat 9 of the cylinder D and the receiving seat 12 of the mount member G come into pressure contact with each other, and the mount member G is pulled so that the instrument F mounted on the mounting portion 13 of the mount member G is fixed in a desired spatial position.

For removing the fixed condition of the instrument F, the switching device B is turned off to cut off the supply of the pressure fluid. As a result, the spring 6 within the cylinder D pushes up the piston 5 to return the reciprocating rod 4. By doing this, the tension of the linear element 14 is slightly loosened to release the pressure contacting condition of the respective pieces 10, so that the mount member G is allowed to move freely.

The adjustment handle 8 threadedly engaged with the lower end of the reciprocating rod 4 is rotated to adjust the degree of tension of the linear element 15 during the position fixing operation.

According to this embodiment, since the instrument mounted on the mount member can be fixed in a desired spatial position merely by turning on/off the switching device with one foot or one hand, it is very convenient in view of use.

[SECOND EMBODIMENT]

Figure 3:
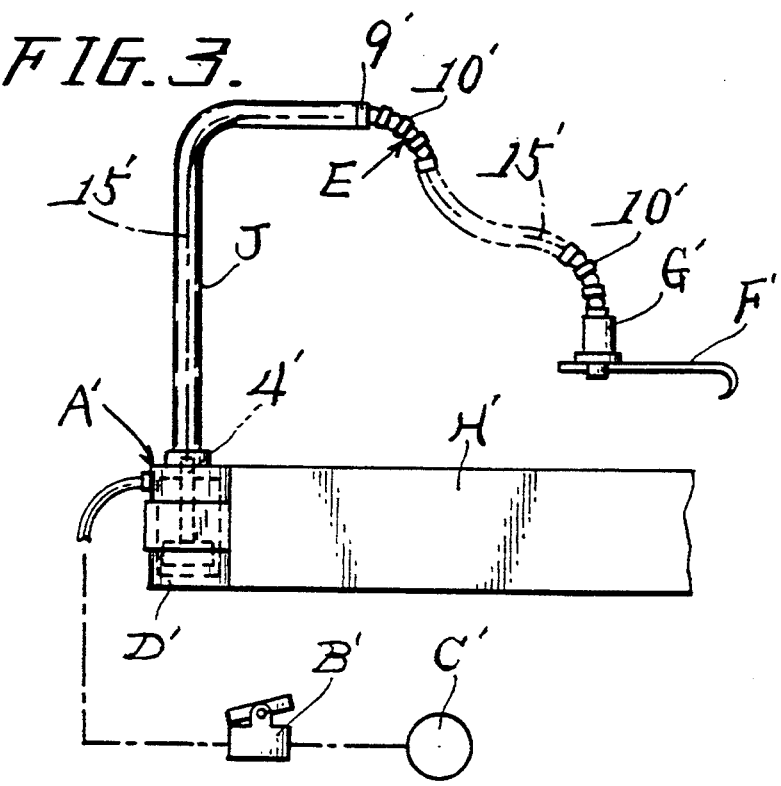
FIG. 3 is an overall view of a second embodiment.

An adjustable position fixing apparatus A' of a second embodiment shown in FIG. 3 has a generally same construction as the first embodiment mentioned above. In this second embodiment, a stationary arm portion J and an adjustable arm portion D' are disposed between a cylinder D' firmly secured to a supporting table H' and a mount member G' on which an instrument F' is mounted.

The cylinder D' is in communication with a pressure fluid supplying machine C' through a switching device B'. The cylinder D' is provided with a cylindrical stationary arm portion J erected from its upper surface. This stationary arm portion J is provided at its distal end with a receiving seat 9'. An adjustable arm portion E' composed of a plurality of pieces 10', 10' as in the first embodiment is disposed between the receiving seat 9' and a receiving seat 12' of the mount member G'. A linear element 15' extends through the stationary arm portion J and adjustable arm portion E' with its one end attached to a reciprocating rod 4' which is disposed within the cylinder D' and with its other end attached to the mount member G'. The operation is the same as the first embodiment.

As in the above embodiment, if the adjustable arm portion E' composed of at least a plurality of pieces 10' is disposed between the cylinder D' and the mount member G', the instrument F', which is mounted on the mount member G', can of course be adjustably fixed to a desired spatial position. Furthermore, it is not essential that the interior of the cylinder is divided into three parts as in the first embodiment as long as a desired tension of the linear member can be obtained.

What is claimed is:

1. An adjustable position fixing apparatus for an instrument, comprising:
   a housing defining a volume:
   a bendable arm extending from said housing;
   means for mounting an instrument on said bendable arm;
   a rod reciprocally movable within said housing;
   a tensionable element extending through said rod and through said bendable arm to said mounting means;
   means for reciprocating said rod within said housing, said reciprocating means including at least one chamber within said housing, at least one piston displaceable within said at least one chamber, and pressure means for supplying a fluid under pressure to said at least one chamber via a flow channel that extends through said rod, said rod being connected to said at least one piston for joint reciprocal movement in response to pressure changes in said at least one chamber; and
   means responsive to said reciprocal movement of said rod in one direction for tensioning said tensionable element and in the other direction for loosening the tension.

2. An apparatus as in claim 1, wherein said bendable arm is comprised of a plurality of arm components connected together in succession in a ball and socket manner, said arm components each having through-going holes through which extends said tensionable element.

3. An apparatus as in claim 1, further comprising a tubular member extending from said housing to said bendable arm, said tensionable element extending through said tubular element as well as through said bendable arm.

4. An apparatus as in claim 1, further comprising an adjustment handle adjustably secured to said rod for displacement relative thereto, said tensionable element having an end secured to said adjustment handle and movable together with said adjustment handle.

5. An apparatus as in claim 1, wherein said bendable arm includes a plurality of elements that come into pressure contact with each other in response to said tensionable element being tensioned for fixing an instrument mounted by said mounting means into a desired spatial position.

6. An adjustable position fixing apparatus for an instrument, comprising:
   a housing defining a volume:
   a bendable arm extending from said housing;
   means for mounting an instrument on said bendable arm;
   a rod reciprocally movable within said housing;
   a tensionable element extending through said rod and through said bendable arm to said mounting means; and
   means for reciprocating said rod within said housing, said reciprocating means including a plurality of axially spaced chambers within said housing, a plurality of axially spaced pistons displaceable within respective ones of said chambers, and pressure means for supplying a fluid under pressure to each of said chambers, said rod being connected to said pistons for joint reciprocal movement in response to presssure changes in said chambers; and means responsive to said reciprocal movement of said rod in one direction for tensioning said tensionable element and in the other direction for loosening the tension.

7. An apparatus as in claim 6, wherein said channels are spaced axially from each other in succession by respective partitions, neighboring ones of said partitions and said pistons being separated from each other in succession by spaces in said channels, said supplying pressure means including a flow channel extending through said rod and being in communication with each of said spaces.

8. An apparatus as in claim 5, wherein said bendable arm includes a plurality of elements that come into pressure contact with each other in response to said tensionable element being tensioned for fixing an instrument mounted by said mounting means into a desired spatial position.

* * * * *